(12) United States Patent
Keall et al.

(10) Patent No.: US 7,668,357 B2
(45) Date of Patent: Feb. 23, 2010

(54) METHOD AND SYSTEM FOR USING COMPUTED TOMOGRAPHY TO TEST PULMONARY FUNCTION

(75) Inventors: Paul John Keall, Richmond, VA (US); Sarang C. Joshi, Chapel Hill, NC (US)

(73) Assignee: Stanford University, Palo Alto, CA (US)

( * ) Notice: Subject to any disclaimer, the term of this patent is extended or adjusted under 35 U.S.C. 154(b) by 590 days.

(21) Appl. No.: 11/250,627

(22) Filed: Oct. 17, 2005

(65) Prior Publication Data
US 2007/0086636 A1   Apr. 19, 2007

(51) Int. Cl.
*G06K 9/00* (2006.01)
(52) U.S. Cl. .................. 382/130; 382/128; 382/131
(58) Field of Classification Search ......... 382/128–134, 382/100; 128/920–925; 250/455.11; 356/39–42; 377/10–12
See application file for complete search history.

(56) References Cited

U.S. PATENT DOCUMENTS

| | | | | |
|---|---|---|---|---|
| 6,249,594 B1 * | 6/2001 | Hibbard | ................ | 382/128 |
| 6,430,430 B1 * | 8/2002 | Gosche | ................ | 600/410 |
| 6,611,630 B1 * | 8/2003 | Miller et al. | ................ | 382/293 |
| 6,901,277 B2 * | 5/2005 | Kaufman et al. | ................ | 600/407 |
| 7,072,706 B2 * | 7/2006 | Baumgardner et al. | ................ | 600/420 |
| 7,106,891 B2 * | 9/2006 | Wyman et al. | ................ | 382/128 |
| 7,130,457 B2 * | 10/2006 | Kaufman et al. | ................ | 382/128 |
| 7,187,810 B2 * | 3/2007 | Clune et al. | ................ | 382/294 |
| 7,206,462 B1 * | 4/2007 | Betke et al. | ................ | 382/280 |
| 2004/0258286 A1 * | 12/2004 | Salla et al. | ................ | 382/128 |
| 2006/0165267 A1 * | 7/2006 | Wyman et al. | ................ | 382/128 |

* cited by examiner

*Primary Examiner*—Samir A. Ahmed
*Assistant Examiner*—Mehdi Rashidian
(74) *Attorney, Agent, or Firm*—Whitham, Curtis, Christofferson & Cook, P.C.

(57) ABSTRACT

Computed axial tomography images of different respiratory phases of lungs are obtained, where the intensity of the image measures lung density. One image is deformed to the coordinate space of the other image, and the differences between the intensity values of the other image as compared to the mapped image are evaluated as measures of ventilation.

14 Claims, 1 Drawing Sheet

METHOD AND SYSTEM FOR USING COMPUTED TOMOGRAPHY TO TEST PULMONARY FUNCTION

STATEMENT OF GOVERNMENT INTEREST

This invention was made with government support under Contract Number CA093626 awarded by the National Institutes of Health. The Government has certain rights in the invention.

BACKGROUND OF THE INVENTION

1. Field of the Invention

The present invention generally relates to methods and systems of determining pulmonary function, and in particular to methods and systems using computed tomography.

2. Background Description

Currently, pulmonary ventilation is performed using single photon emission computed tomography (SPECT), a nuclear medicine imaging procedure, which is more expensive and time consuming than computed axial tomography (CAT scan, or CT). Furthermore, the resolution of SPECT is significantly poorer than that of CT. What is needed is a method for measuring lung ventilation that uses CT.

SUMMARY OF THE INVENTION

It is therefore an object of the present invention to measure pulmonary function using computed axial tomography (CT).

This invention brings together two emerging technologies, thoracic four dimensional computed tomography (4DCT) and deformable image registration algorithms, to devise a new clinical test for lung function. The lung function tests will show the difference in lung density between respiratory phases in different parts of the lung, from which regions of small or no density change (low ventilation) can be identified.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

Figure 1:
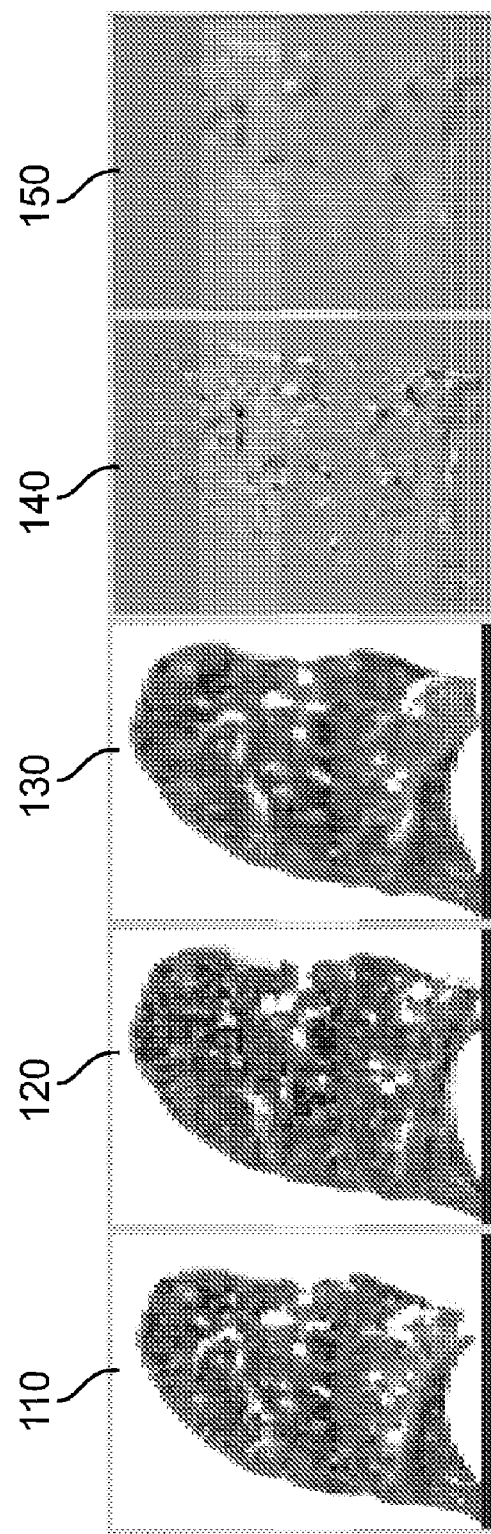
FIG. 1 shows an exhale image 110; an inhale image 120; the exhale image deformed 130 to the inhale image; a difference image 140 between the inhale image and the deformed exhale image; and a smoothed difference image 150.

Four-dimensional computed tomography (4DCT) acquisition methods that explicitly account for respiratory motion have been recently developed in academic and commercial settings. Similarly, deformable image registration algorithms are evolving to the point of routine clinical utility. The combination of these two emerging technologies can be used as a pulmonary function test for ventilation by assessing the density differences of the same anatomic areas of the lung from CT scans acquired at different respiratory phases.

Due to the deformation of the lungs caused by respiration, the CT scans at different respiratory phases (referred to subsequently as inhale and exhale scans) cannot be directly compared as the anatomy is in a different location in the two images. FIGS. 1a and 1b, respectively, show exhale 110 and inhale 120 images. However, deformable image registration algorithms can be applied to deform one respiratory phase to another. This is shown by the image 130 in FIG. 1c, where the exhale image 110 of FIG. 1a is deformed into the inhale image 120 of FIG. 1b. This enables calculation of the density differences between the inhale image 120 (shown in FIG. 1b) and the deformed exhale image 130 (shown in FIG. 1c) based on the differences of the intensity values in the images, and hence ventilation can be quantified.

For example, let the exhale CT scan be given by $I(x_{exhale})$, and the inhale scan by $I(x_{inhale})$. A transformation, u, can be found that maps the coordinate space of $I(x_{exhale})$ to $I(x_{inhale})$ via $u(x_{exhale} \rightarrow x_{inhale})$. The ventilation can then be quantified by evaluating the difference between the two images $I(x_{inhale}) - I(u(x_{exhale}))$ in the lung region.

Note that the vector displacement fields themselves, and variations thereof, could also be used to analyze lung function. Furthermore, for this method it is prudent to use a deformable image registration algorithm which is not driven by minimizing intensity differences, as such algorithms will artificially try to minimize the intensity difference, which for this application is the quantity of interest.

A proof-of-principle example of this method is given in FIG. 1 in which the exhale image 110 has been deformed to the inhale image 120 creating the image 130 shown in FIG. 1. A subtraction of the deformed exhale image 130 from the inhale image 120 results in a difference image 140. A smoothing function is then applied to minimize the effects of CT artifacts and limitations in the image registration process, resulting in a smoothed difference image 150.

While the invention has been described in terms of a single preferred embodiment, those skilled in the art will recognize that the invention can be practiced with modification within the spirit and scope of the appended claims.

Having thus described our invention, what we claim as new and desire to secure by Letters Patent is as follows:

1. A method for quantifying pulmonary ventilation, comprising:
    obtaining via a computed axial tomography (CT) device images of a lung in first and second respiratory phases;
    deforming an image of the first respiratory phase to an image of the second respiratory phase, said deforming using deformable image registration algorithm; and
    quantifying differences in density of corresponding anatomical areas of the lung between the deformed first phase image and the second phase image as a measure of pulmonary ventilation between said first and second respiratory phases.

2. The method of claim 1, wherein the quantified differences in lung density are measured by image intensity.

3. The method of claim 1, wherein the deformable image registration algorithm is not driven by minimizing differences in image intensity.

4. The method of claim 1, further comprising smoothing the differences between the deformed first phase image and the second phase image before quantifying the differences.

5. The method of claim 1, wherein said first phase is an exhale phase and said second phase is an inhale phase.

6. The method of claim 1, wherein the deforming is accomplished using a transformation that maps a coordinate space of the first phase image to a coordinate space of the second phase image.

7. The method of claim 6, wherein the quantifying is accomplished by evaluating the differences between image intensity values in the coordinate space of the second phase image as compared to the mapped first phase image.

8. A system for quantifying pulmonary ventilation, comprising:

means for obtaining computed axial tomography (CT) of a lung in first and second respiratory phases;

means for deforming an image of the first respiratory phase to an image of the second respiratory phase, said deforming using deformable image registration algorithm; and means for quantifying differences in density of corresponding anatomical areas of the lung between the deformed first phase image and the second phase image as a measure of pulmonary ventilation between said first and second respiratory phases.

9. The system of claim 8, wherein the quantified differences in lung density are measured by image intensity.

10. The system of claim 9, wherein the deformable image registration algorithm is not driven by minimizing differences in image intensity.

11. The system of claim 8, further comprising means for smoothing the differences between the deformed first phase image and the second phase image before quantifying the differences.

12. The system of claim 8, wherein said first phase is an exhale phase and said second phase is an inhale phase.

13. The system of claim 8, wherein the deforming means uses a transformation that maps a coordinate space of the first phase image to a coordinate space of the second phase image.

14. The system of claim 13, wherein the quantifying means evaluates the differences between image intensity values in the coordinate space of the second phase image as compared to the mapped first phase image.

* * * * *